United States Patent
Rousseau

(10) Patent No.: US 7,232,454 B2
(45) Date of Patent: Jun. 19, 2007

(54) SURGICAL WOUND CLOSURE/TRANSFER MARKING DEVICE

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 534 days.

(21) Appl. No.: 10/674,611

(22) Filed: Sep. 29, 2003

(65) Prior Publication Data

US 2005/0070956 A1    Mar. 31, 2005

(51) Int. Cl.
*A61B 17/08* (2006.01)
*A61D 1/00* (2006.01)

(52) U.S. Cl. ......................... 606/213; 602/58
(58) Field of Classification Search ............... 606/213, 606/215, 216; 602/42–58
See application file for complete search history.

(56) References Cited

U.S. PATENT DOCUMENTS

| | | | |
|---|---|---|---|
| 889,662 A | 6/1908 | Coulter | |
| 3,060,932 A | 10/1962 | Pereny et al. | |
| 3,611,842 A | 10/1971 | Skipper | |
| 3,926,193 A | 12/1975 | Hassson | |
| 3,933,158 A | 1/1976 | Haverstock | |
| 3,971,384 A | 7/1976 | Hasson | |
| 4,038,989 A | 8/1977 | Romero-Sierra et al. | |
| 4,114,624 A | 9/1978 | Haverstock | |
| 4,212,305 A | 7/1980 | Lahay | |
| 4,222,383 A | 9/1980 | Schossow | |
| 4,524,767 A | 6/1985 | Glassman | |
| 4,531,521 A * | 7/1985 | Haverstock | 606/215 |
| 4,732,146 A | 3/1988 | Fasline | |
| 4,825,866 A | 5/1989 | Pierce | |
| 4,899,762 A | 2/1990 | Muller | |
| 4,976,726 A | 12/1990 | Haverstock | |
| 5,156,431 A | 10/1992 | Lowe | |
| 5,197,493 A | 3/1993 | Grier-Idris | |
| 5,259,835 A | 11/1993 | Clark et al. | |
| 5,263,970 A | 11/1993 | Preller | |
| 5,300,065 A | 4/1994 | Anderson | |
| 5,336,219 A | 8/1994 | Krantz | |
| 5,514,148 A | 5/1996 | Smith | |
| 5,562,705 A | 10/1996 | Whiteford | |

(Continued)

FOREIGN PATENT DOCUMENTS

EP    0 341 045 A2    11/1989

(Continued)

OTHER PUBLICATIONS

International Search Report dated Jan. 25, 2005, for corresponding application PCT/US2004/030808.

(Continued)

*Primary Examiner*—Anhtuan T. Nguyen
*Assistant Examiner*—Natalie Pous

(57) ABSTRACT

The present invention is directed to a multi-functional surgical wound closure/transfer marking device comprising a substrate having a proximal surface, a distal surface and markings; an adhesive layer having a proximal surface, a distal surface and being disposed on the proximal surface of substrate; and a primary release sheet having a proximal surface and a distal surface, being in two portions that are disposed releasably adherently to the proximal surface of the adhesive layer. The device has transferable markings on the proximal surface of the second portion of the primary release sheet, where the transferable markings are substantially aligned with the markings on the substrate.

9 Claims, 1 Drawing Sheet

U.S. PATENT DOCUMENTS

| | | |
|---|---|---|
| 5,611,794 A | 3/1997 | Sauer et al. |
| 5,752,973 A | 5/1998 | Kieturakis |
| 5,803,086 A | 9/1998 | Scholz et al. |
| 5,893,879 A | 4/1999 | Hirshowitz et al. |
| 5,972,021 A | 10/1999 | Huttner et al. |
| 5,979,450 A | 11/1999 | Baker et al. |
| 6,007,564 A * | 12/1999 | Haverstock ............... 606/216 |
| 6,042,599 A | 3/2000 | Huttner et al. |
| 6,120,525 A | 9/2000 | Westcott |
| 6,494,896 B1 | 12/2002 | D'Alessio et al. |
| 6,742,522 B1 * | 6/2004 | Baker et al. ............. 128/849 |
| 2002/0065534 A1 | 5/2002 | Hermann et al. |
| 2003/0050590 A1 | 3/2003 | Kirsch |
| 2005/0034731 A1 * | 2/2005 | Rousseau et al. .......... 128/849 |
| 2005/0034732 A1 * | 2/2005 | Rousseau et al. .......... 128/849 |

FOREIGN PATENT DOCUMENTS

| | | |
|---|---|---|
| EP | 0 396 274 A1 | 11/1990 |

OTHER PUBLICATIONS

Donatas Satas, Handbook of Pressure Sensitive Adhesive Technology, 1989, chapter 23, Van Nostrand Reinhold, NY.

* cited by examiner

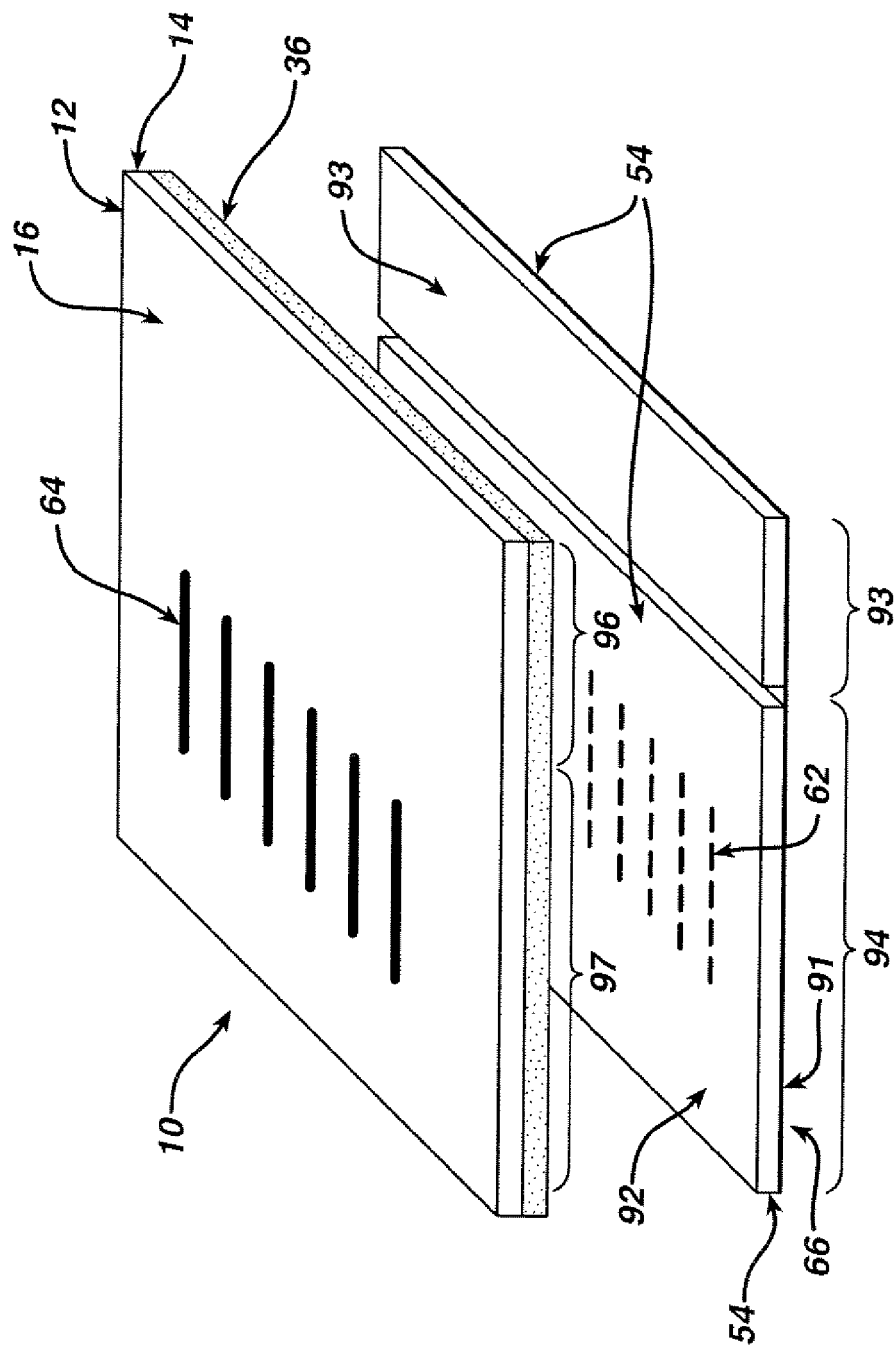

SURGICAL WOUND CLOSURE/TRANSFER MARKING DEVICE

FIELD OF INVENTION

The present invention relates to a surgical wound closure/transfer marking device that is multi-functional and that provides medical practitioners with a device that enables alignment and approximation of the edges of the incision during closure, serves as the primary means of closure of the incision, and serves as a protective wound dressing post surgically.

BACKGROUND OF THE INVENTION

Following a surgical procedure, a wound is often closed with a plurality of sutures or staples, and a wound dressing is applied. Therefore, surgical procedures often utilize several medical devices to close the wound and protect the incision during healing. Multi-functional medical devices performing two or three functions selected from a sterile surgical drape, an incision approximation device, a wound closure device and a sterile dressing, have been described in the prior art. For example, U.S. Pat. No. 4,899,762 discloses a combination surgical drape, dressing and closure device, which includes a combination drape/dressing having a central dressing portion, which may have an incision guide line, and peripheral drape portions which are secured together with a weakened tear line. This reference also teaches a straddling closure that is utilized in conjunction with the combination drape/dressing which may be integral or separate from the combination drape/dressing.

Additionally, U.S. Pat. Nos. 4,222,383 and 4,976,726 describe multi-functional devices that may perform the dual functions of a surgical drape and wound closure device. U.S. Pat. Nos. 4,114,624 and 4,531,521 describe surgical wound devices that perform the dual functions of being a template for incision and a wound closure device. U.S. Pat. No. 6,007,564 discloses the use of several devices to perform (i) the dual functions of being a drape and a dressing, and (ii) a wound closure device.

However, there are disadvantages associated with the devices described in the prior art. For example, as shown in FIGS. 6–8 of U.S. Pat. No. 4,899,762, this reference teaches a multiple layer dressing that comprises two adhesive layers and two substrates over the incision after completion of the surgical procedure. This multiple layer structure remaining over the incision severely impedes the transmission of water vapor from the skin tissue and increases the chance of skin maceration. U.S. Pat. No. 4,222,383 does not perform the functions of an incision approximation device and a dressing. U.S. Pat. Nos. 4,114,624 and 4,531,521 describes devices that limit the type of incision that may be made by a physician and require the device to be placed with some degree of accuracy over the targeted incision site since the device functions as an incision template. The disadvantage associated with U.S. Pat. No. 4,976,726 is that the sheet that may function as a drape is not removed from the incision site after the surgical procedure and the closure means is placed directly upon a contaminated surface. In addition, a multiple layer structure remains over the incision after the surgical procedure, which severely impedes the transmission of water vapor from the skin tissue and increases the chance of skin maceration. U.S. Pat. No. 6,007,564 requires the use of multiple devices to perform the various functions.

While these previous disclosures teach multi-functional surgical devices, there is still a need for a multi-functional device that is simple to use and that performs additional functions. Specifically, it is desirable to have a surgical wound closure/transfer marking device without the disadvantages described above, that performs the functions of an incision approximation device, a closure device and a sterile dressing, and that does not significantly impede the natural water vapor transmission of the skin tissue.

SUMMARY OF THE INVENTION

The present invention is directed to a multi-functional surgical wound closure/transfer marking device comprising a substrate having a proximal surface, a distal surface and markings; an adhesive layer having a proximal surface, a distal surface and being disposed on the proximal surface of substrate; and a primary release sheet having a proximal surface and a distal surface, being in two portions that are disposed releasably adherently to the adhesive layer. The device has transferable markings on the proximal surface of the second portion of the primary release sheet, where the transferable markings are substantially aligned with the markings on the substrate.

Once the practitioner has completed the surgical procedure, the practitioner is able to align and approximate the edges of the incision by aligning the alignment markings on the substrate with the transferable markings that were transferred to the skin of the patient earlier, and to close the incision by applying the substrate with the adhesive layer to the clean surface of the skin. The substrate with the adhesive then serves as the dressing during the healing process.

DESCRIPTION OF THE DRAWING

The FIGURE is an exploded perspective view of an embodiment of a surgical wound closure/transfer marking device of the present invention.

DETAILED DESCRIPTION OF THE INVENTION

A convention followed in this description is that the side of the device closest to the patient, when the device is placed on the skin of the patient as described herein, is referred to as "proximal" and the side furthest away from the patient is referred to as "distal".

Referring to the FIGURE, the surgical wound closure/transfer marking device 10 includes a substrate 12 having a proximal surface 14, a distal surface 16 and markings 64; an adhesive layer 36 being disposed on the proximal surface 14 of substrate and having a first portion 96 and a second portion 97; and a primary release sheet 54 having a proximal surface 91, a distal surface 92, a first portion 93 and a second portion 94, where the first and second portions may optionally be detachable from each other and are disposed releasably adherently to the first and second portions 96 and 97, respectively, of adhesive layer 36. Device 10 has transferable markings 62 on proximal surface 91 of second portion 94 of primary release sheet 54, where transferable markings 62 are substantially aligned with markings 64 on substrate 12.

Device 10 may include an optional secondary release sheet disposed proximally to proximal surface 91 of primary release sheet 54 to prevent markings 62 from transferring prematurely. For example, the secondary release sheet may optionally be in two portions that may be detachable from each other, with one portion being adjacent to first portion 93 of primary release sheet 54 and the other portion being adjacent to second portion 94 of primary release sheet 54.

Substrate 12, adhesive layer 36, primary release sheet 54 and any optional layer may be sized to substantially conform to each other and may be joined together, for example, by any technique used for making book-like arrangements.

In general, the embodiment described in FIG. 1 may be utilized in the following manner. Proximal surface 91 of primary release sheet 54 is exposed. First portion 93 of primary release sheet 54 may be removed at a perforation, for example, to expose a first portion 96 of adhesive layer 36. The practitioner places device 10 on the skin of the patient, using first portion 96 of adhesive layer 36 to adhere device 10 to the skin. Markings 62 may then be transferred from device 10 to create or transfer markings on the skin by contacting proximal surface 91 of second portion 94 of primary release sheet 54 with the skin in the area where a surgical incision is planned. Substrate 12, second portion 97 of adhesive layer 36 and second portion 94 of primary release sheet 54 may then be bent over that portion of device 10 that is adhered to the skin. The practitioner performs a surgical procedure by making an incision in skin of the patient. Following completion of the surgical procedure, second portion 94 of primary release sheet 54 may be removed to expose second portion 97 of adhesive layer 36; markings 64 on substrate 12 may be aligned with the markings on the skin; second portion 97 of adhesive layer 36 may be contacted with the skin to close the surgical incision; leaving substrate 12 and adhesive layer 36 covering the surgical incision.

Substrate 12 may be flexible and may be a woven or non-woven material, suitable for example for a dressing or bandage, or a film formed from a transparent or translucent polymeric material. The material preferably allows for moisture evaporation through substrate 12 during the incision healing process. In combination with adhesive layer 36, substrate 12 preferably has a moisture vapor transmission rate of at least about 300 $g/m^2/24$ hrs. Suitable materials include, but are not limited to polyurethane film such as "MediFilm 437" (Mylan Technologies, St. Albans, Vt.), polyolefin films, such as low density polyethylene film such as "CoTran" polyethylene film (3M, Minneapolis, Minn.), copolyester film such as "MediFilm 390" (Mylan Technologies, St. Albans, Vt.), polyether polyamides such as "MediFilm 810" (Mylan Technologies, St. Albans, Vt.) and the like. Substrate 12 is preferably formed from a copolyester such as a polyetherpolyester. Generally, substrate 12 and adhesive layer 36 separate from the patient's skin 46 as the patient's skin regenerates and dead skin adhering to adhesive layer 36 sloughs off. Alternatively, proximal surface 14 of substrate 12 may be coated with an absorbable polymer composition including, but not limited to, glycolide, lactide, copolymers of glycolide, copolymers of glycolide and lactide, polydioxanone, polycaprolactone, polypeptide, cellulosic and derivatives thereof. As the absorbable polymer degrades, substrate 12 separates from adhesive layer 36. Therefore, by controlling the absorption rate of the absorbable polymer, it is possible to control the length of time substrate 12 adheres to adhesive layer 36, for example, in those cases where it is desirable to separate substrate 12 from adhesive layer 36 prior to the length of time it would take for the patient's skin to regenerate and slough off adhesive layer 36. As an alternative, substrate 12 may be formed from any material exhibiting the moisture vapor transmission rate described above and that is solvent releasable from adhesive layer 36, or from a class of materials that expand or contract when triggered by tiny changes in temperature, light, a solvent, or other stimulus, referred to as "smart" gels, and described in U.S. Pat. Nos. 4,732,930, 5,403,893, 5,580,929, and U.S. Reissue No. 35,068.

Adhesive layer 36 may be formed from one or more adhesive materials that include, but are not limited to, acrylic copolymer, polyisobutylene, polyurethane, polymeric silicone and rubber-based hotmelts. Adhesive layer 36 may comprise two or more adhesive materials in a stacked arrangement, or may be different adhesive materials arranged in parallel strips to one another. Specifically, both proximal surface and distal surface of adhesive layer 36 are adhesive. The thickness of adhesive layer 36 may be about 0.0015 to about 0.003 inches and may have a peel strength between about 10 and 50 oz/in when tested according to ASTM 3330 on a low density polyethylene panel. Additionally, the adhesive preferably may have a cohesive strength of at least 50 hours, more preferably at least 80 hours, when tested according to ASTM 3654 at 2 psi shear pressure. The adhesive is substantially impermeable to liquid water, but preferably has a moisture vapor transmission rate greater than about 250 $g/m^2/24$ hr. Preferably, adhesive layer 36 is formed from an acrylic copolymer with a moisture transmission rate of about 300 $g/m^2/24$ hr such as an acrylic copolymer adhesive that is available from National Starch, Bridgewater, N.J., under the tradename "DuroTak" (#80-147A). Alternatively, the adhesive layer may be a "double-sided tape" comprising a substrate material coated on both surfaces with one or more of the adhesives described above.

Primary release sheet 54 may be formed from materials including, but not limited to, Kraft paper, polyethyleneterephthalate (PET), polypropylene and the like. Preferably primary release sheet 54 is formed from Kraft paper with a release coating applied to the distal surface thereof so that the primary release sheet is readily removed from the proximal surface of adhesive layer 36, so that device 10 may be adhered to the skin of the patient. The release coating applied to the distal surface of release sheet 54 is preferably categorized as a "low release" coating as defined in the *Handbook of Pressure Sensitive Adhesive Technology*, Release Coating, Chapter 23. This definition requires a release value less than about 35 g/in. Materials suitable for forming release coatings include, but are not limited to, hydrocarbon waxes, silicone polymers, polyolefins, fluorocarbon copolymers and polyvinyl carbamates. Preferably, the distal surface of release sheet 54 is coated with less than about 3 $g/m^2$ of a silicone polymer.

Secondary release sheet 66 may be formed from materials including, but not limited to, Kraft paper, polyethyleneterephthalate (PET), polypropylene and the like. Secondary release sheet 66 may be releasably adherent, for example, by Van der Waals forces to proximal surface 14 of primary release sheet 54.

Preferably, adhesive layer 36 also includes a sufficient quantity of an antimicrobial agent to substantially inhibit the growth of microorganisms on the skin of the patient adjacent said adhesive. Suitable antimicrobial agents include, but are not limited to, a compound selected from the group consisting of 2,4,4'-Arichloro-2'hydroxydiphenyl ether, benzalkonium chloride, silver sulfadiazine and povidone iodine. The preferred antimicrobial agent is 2,4,4'-trichloro-2'hydroxydiphenyl ether with a concentration (w/w) in adhesive material from between about 0.1% to about 5.0% of the adhesive. A more preferred concentration of the preferred 2,4,4'-trichloro-2'hydroxydiphenyl ether is between about 1% and about 2%. A determination of a zone of inhibition in a standard plating experiment with the preferred acrylic copolymer adhesive having a concentration of the preferred 2,4,4'-trichloro-2'hydroxydiphenyl ether of 1.25% w/w shows a zone of inhibition of 4 mm against gram positive microorganisms.

Any therapeutic agent may be incorporated into adhesive layer 36, substrate 12 or a reservoir layer therebetween. Examples of such therapeutic agents include, but are not limited to anti-inflammatory agents (steroidal, non-steroidal, etc. such as but not limited to celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam), anesthetic agents (channel blocking agents, lidocaine, bupivacaine, mepivacaine, procaine, chloroprocaine, ropivacaine, tetracaine, prilocaine, levobupivicaine, and combinations of local anesthetics with epinephrine etc.), antiproliferatives (rapamycin, etc.), growth factors (PGDF, etc.), scar treatment agents (hylauronic acid), angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, Ioratidine, aurothioglucose, auranofin, Cortisol (hydrocortisone), cortisone, fludrocortisone, prednisone, prednisolone, 6α-methylprednisone, triamcinolone, betamethasone, and dexamethasone.

Preferably, device 10 is placed in a package formed from materials substantially resistant to the passage of microorganisms and exposed to conditions that render any microorganisms therewithin substantially non-viable. Suitable materials for forming the package include, but are not limited to, paper, non-wovens, polymeric films, metallic foils and composites of these materials. Suitable conditions for rendering microorganisms non-viable include, but are not limited to, ethylene oxide gas exposure, gaseous hydrogen peroxide exposure and exposure to ionizing radiation such as UV, electron beam and gamma. The device of the invention when packaged and exposed to suitable conditions for rendering microorganisms non-viable under controlled conditions may generally considered as "sterile" as long as the package is intact. When selecting materials for forming device 10, its packaging and sterilization techniques, consideration should be given to the materials selected and their compatability with the sterilization technique.

Under normal conditions, the adhesive layer retains the substrate over the healing surgical incision for about 5–7 days, substantially preventing dehiscence of the incision and allowing healing. Additionally, since the adhesive layer and the substrate allow transmission of water vapor therethrough, the occurrence of maceration around the incision is substantially reduced.

Preferably, the wound closure device of the invention is substantially rectangular, being sized from between about two inches by four inches to about ten inches by twelve inches. However, the wound closure device of the invention may be prepared in a variety of sizes and shapes for particular applications, including but not limited to, smaller sizes for closing trocar openings resulting from minimally invasive surgery procedures.

What is claimed:

1. A surgical wound closure/transfer marking device comprising:
    a substrate having a proximal surface, a distal surface and markings;
    an adhesive layer disposed on the proximal surface of substrate and having a first portion and a second portion;
    a primary release sheet having a proximal surface, a distal surface, a first portion, a second portion and markings on the proximal surface of the second portion of the primary release sheet, where the first and second portions are disposed releasably adherently to the first and second portions, respectively, of adhesive layer and the markings on the proximal surface of the second portion of the primary release sheet are substantially aligned with the markings on the substrate; and
    a secondary release sheet being disposed on the proximal surface of the primary release sheet.

2. The surgical wound closure/transfer marking device of claim 1, where the first and second portions of the primary release sheet are detachable from each other.

3. The surgical wound closure/transfer marking device of claim 1, where the substrate, adhesive layer and primary release sheet are joined in a book-like arrangement.

4. The surgical wound closure/transfer marking device of claim 3, wherein the substrate and the adhesive layer are size to substantially conform to each other.

5. The surgical wound closure/transfer marking device of claim 1, wherein the substrate is formed from a material selected from the group consisting of polyurethane, polyolefins, copolyesters and polyether polyamides.

6. The surgical wound closure/transfer marking device of claim 1, wherein the adhesive layer is formed from an adhesive material selected from the group consisting of acrylic copolymer, polyisobutylene, polyurethane, polymeric silicone and rubber-based hotmelts.

7. The surgical wound closure/transfer marking device of claim 1, wherein the adhesive layer or substrate comprises a sufficient quantity of an antimicrobial agent to substantially inhibit the growth of microorganisms on the skin of the patient adjacent said adhesive.

8. The surgical wound closure/transfer marking device of claim 7, wherein said antimicrobial agent is a compound selected from the group consisting of 2,4,4'-trichloro-2'hydroxydiphenyl ether, benzalkonium chloride, silver sulfadiazine and povidone iodine.

9. A surgical procedure comprising the steps of:
    providing a surgical wound closure/transfer marking device comprising a substrate having a proximal surface, a distal surface and markings; an adhesive layer disposed on the proximal surface of substrate and having a first portion and a second portion; and a primary release sheet having a proximal surface, a distal surface, a first portion, a second portion and markings on the proximal surface of the second portion of the primary release sheet, where the first and second portions are disposed releasably adherently to the first and second portions, respectively, of adhesive layer and the markings on the proximal surface of the second portion of the primary release sheet are substantially aligned with the markings on the substrate;
    removing the first portion of primary release sheet to expose the first portion of the adhesive layer;
    placing the first portion of the adhesive layer on the skin of a patient;
    contacting the proximal surface of the second portion of the primary release sheet with the skin in the area where a surgical incision is planned to transfer the markings from the proximal surface of the second portion of the primary release sheet onto the skin;
    bending the substrate, the second portion of the adhesive layer and the second portion of primary release sheet over that portion of the device that is adhered to the skin;

making the surgical incision in skin of the patient and performing a surgical procedure;
removing the second portion of the primary release sheet to expose the second portion of the adhesive layer;
aligning the markings on the substrate with the markings on the skin; and
contacting the second portion of the adhesive layer with the skin to close the surgical incision thereby leaving the substrate and the adhesive layer covering the surgical incision.

* * * * *